(12) United States Patent
Cantore et al.

(10) Patent No.: US 11,957,747 B2
(45) Date of Patent: *Apr. 16, 2024

(54) VECTOR PRODUCTION

(71) Applicants: Ospedale San Raffaele S.r.l., Milan (IT); Fondazione Telethon ETS, Rome (IT)

(72) Inventors: Alessio Cantore, Milan (IT); Angelo Leone Lombardo, Milan (IT); Luigi Naldini, Milan (IT)

(73) Assignees: Ospedale San Raffaele S.r.l., Milan (IT); Fondazione Telethon ETS, Rome (IT)

( * ) Notice: Subject to any disclaimer, the term of this patent is extended or adjusted under 35 U.S.C. 154(b) by 241 days.

This patent is subject to a terminal disclaimer.

(21) Appl. No.: 17/143,953

(22) Filed: Jan. 7, 2021

(65) Prior Publication Data

US 2021/0346489 A1    Nov. 11, 2021

Related U.S. Application Data

(63) Continuation of application No. 15/325,124, filed as application No. PCT/IB2015/055286 on Jul. 13, 2015, now Pat. No. 10,912,824.

(30) Foreign Application Priority Data

Jul. 14, 2014   (GB) .................................. 1412494

(51) Int. Cl.
*A61K 39/12* (2006.01)
*C12N 7/04* (2006.01)
*C12N 15/86* (2006.01)

(52) U.S. Cl.
CPC ............... *A61K 39/12* (2013.01); *C12N 7/04* (2013.01); *C12N 15/86* (2013.01); *A61K 2121/00* (2013.01); *C12N 2740/10052* (2013.01); *C12N 2740/16041* (2013.01); *C12N 2740/16052* (2013.01)

(58) Field of Classification Search
None
See application file for complete search history.

(56) References Cited

U.S. PATENT DOCUMENTS 8,236,771 B2    8/2012   Cicciarelli et al.
10,912,824 B2 *  2/2021   Cantore ................. A61P 19/02
2005/0287129 A1  12/2005  Cicciarelli et al.

FOREIGN PATENT DOCUMENTS

CN    1321165 A    11/2001
CN    1554764 A    12/2004
(Continued)

OTHER PUBLICATIONS

Haga K, et al. Permanent, lowered HLA class I expression using lentivirus vectors with shRNA constructs: Averting cytotoxicity by alloreactive T lymphocytes. Transplant Proc. Dec. 2006;38(10):31 (Year: 2006).*

(Continued)

*Primary Examiner* — Michelle S Horning
(74) *Attorney, Agent, or Firm* — MARSHALL, GERSTEIN & BORUN LLP (57) ABSTRACT

An enveloped viral particle producer or packaging cell, wherein the cell is genetically engineered to decrease expression of MHC-I on the surface of the cell.

14 Claims, 5 Drawing Sheets

Specification includes a Sequence Listing.

(56) References Cited

FOREIGN PATENT DOCUMENTS

| | | |
|---|---|---|
| EP | 2339010 A2 | 6/2011 |
| JP | 2013-538562 A | 10/2013 |
| WO | WO-96/007749 A2 | 3/1996 |
| WO | WO-97/02355 A1 | 1/1997 |
| WO | WO-98/05635 A1 | 2/1998 |
| WO | WO-98/07859 A2 | 2/1998 |
| WO | WO-98/09985 A2 | 3/1998 |
| WO | WO-98/17815 A1 | 4/1998 |
| WO | WO-00/08043 A2 | 2/2000 |
| WO | WO-2012/012667 A2 | 1/2012 |
| WO | WO-2012/145384 A1 | 10/2012 |

OTHER PUBLICATIONS

Hacke K, Falahati R, Flebbe-Rehwaldt L, Kasahara N, Gaensler KM. Suppression of HLA expression by lentivirus-mediated gene transfer of siRNA cassettes and in vivo chemoselection to enhance hematopoietic stem cell transplantation. Immunol Res. 2009;44(1-3):112-26. (Year: 2009).*

Lund et al., Pseudovirions as vehicles for the delivery of siRNA, Pharm. Res., 27(3):400-20 (Mar. 2010).

Adams et al., The Adaptable Major Histocompatibility Complex (MHC) Fold: Structure and Function of Nonclassical and MHC Class I-like Molecules, Annual Review Immunology, vol. 31, pp. 529-536 (2013).

Aiuti et al., Gene Therapy for Immunodeficiency Due to Adenosine Deaminase Deficiency, New England Journal Medicine, vol. 360, pp. 447-458 (2009).

Aiuti et al., Lentiviral hematopoietic stem cell gene therapy in patients with Wiskott-Aldrich syndrome, Science, vol. 341, No. 6148, p. 1233151 (2013).

Arthur et al., Cellular proteins bound to immunodeficiency viruses: implications for pathogenesis and vaccines, Science, 258(5090):1935-8 (Dec. 1992).

Arthur et al., Macaques immunized with HLA-DR are protected from challenge with simian immunodeficiency virus, J. Virol., 69(5):3117-24 (May 1995).

Ausubel et al., Current Protocols in Molecular Biology, John Wiley and Sons, chapters 9, 13, 16 (1995).

Biffi et al., Lentiviral hematopoietic stem cell gene therapy benefits metachromatic leukodystrophy, Science, vol. 341, pp. 1233158 (2013).

Bobis-Wozowicz et al., Non-integrating gamma-retroviral vectors as a versatile tool for transient zinc-finger nuclease delivery, Scientific Reports, 4, article No. 4656 (2014).

Boztug et al., Stem-cell Gene Therapy for the Wiskott-Aldrich Syndrome, New England Journal Medicine, vol. 363, pp. 1918-1927 (2010).

Cantore et al., Hyperfunctional coagulation factor IX improves the efficacy of gene therapy in hemophilic mice, Blood, vol. 120, No. 23, pp. 4517-4520 (2012).

Cantore et al., Liver-directed lentiviral gene therapy in a dog model of hemophilia B, Science Translational Medicine, 7, 277ra28 (2015).

Cartier et al, Hematopoietic stem cell gene therapy with a lentiviral vector in X-linked adrenoleukodystrophy, Science, vol. 326, No. 5954, pp. 818-823 (2009).

Coffin et al., Retorviruses, Cold Spring Harbour Laboratory Press, pp. 758-763 (1997).

European Patent Application No. 15757332.0, Communication Pursuant to Article 9493) EPC, dated Jan. 29, 2020.

Follenzi et al., HIV-based vectors. Preparation and use, Methods Mol. Med, vol. 69, pp. 259-274 (2002).

Gait, Oligonucleotide Synthesis: A Practical Approach, IRL Press (1984).

Gaj et al, ZFN, TALEN and CRISPR/Cas-based methods for genome engineering, Trends Biotechnol., vol. 31, pp. 397-405 (2013).

GenBank Accession No. NM_004048, May 3, 2014.

Hacein-Bey-Abina et al., Efficacy of Gene Therapy for X-Linked Severe Combined Immunodeficiency, New England Journal Medicine, vol. 363, No. 4, pp. 355-364 (2010).

Hsu et al, Development and applications of CRISPR-Cas9 for genome engineering, Cell, vol. 157, pp. 1262-1278 (2014).

International Search Report and Written Opinion, International Application No. PCT/IB2015/0555286, dated Nov. 24, 2015.

Japanese Patent Application No. 2017-502253, Notice of Reasons for Refusal, dated May 14, 2019.

Leavitt et al., Human immunodeficiency virus type 1 integrase mutants retain in vitro integrase activity yet fail to integrate viral DNA efficiently during infection, J. Virol., vol. 70, pp. 721-728 (1996).

Lewis et al., Human immunodeficiency virus infection of cells arrested in the cell cycle, EMBO J, vol. 11, pp. 3053-3058 (1992).

Lewis et al., Passage through mitosis is required for oncoretroviruses but not for the human immunodeficiency virus, J. Virol., vol. 68, pp. 510-516 (1994).

Lilley et al. (eds.), Methods in Enzymology: DNA Structures Part A: Synthesis and Physical Analysis of DNA, vol. 2011, Academic Press (1992).

Lombardo et al, Site-specific integration and tailoring of cassette design for sustainable gene transfer, Nat Methods, vol. 8 pp. 861-869 (2011).

Maetzig et al., Retroviral protein transfer: falling apart to make an impact, Current Gene Ther., vol. 12, pp. 389-409 (2012).

Markusic, High-efficiency transduction and correction of murine hemophilia B using AAV2 vectors devoid of multiple surface-exposed Tyrosines, Molecular Therapy, vol. 18, No. 12, pp. 2048-2056 (2010).

Matsui et al., A microRNA-regulated and GP64-pseudotyped lentiviral vector mediates stable expression of FVIII in a murine model of Hemophilia A, Mol. Ther., vol. 19 No. 4 pp. 723-730 (2011).

Matucci et al., HLA-C increases HIV-1 infectivity and is associated with gp120, Retrovirology, 5:68 (Aug. 2008).

McDevitt, Discovering the role of the major histocompatibility complex in the immune response, Annu Rev Immunol, vol. 18, pp. 1-17 (2000).

Meng et al., Construction and identification of mouse beta2m sense and antisense RNA expression vectors, Academic Journal of Sun Yat-sen University of Medical Sciences, Dec. 31, 2001, vol. 66, No. 6, abstract.

Naldini et al., Efficient transfer, integration, and sustained long-term expression of the transgene in adult rat brains injected with a lentiviral vector, Proc Natl Acad Sci USA, vol. 93, pp. 11382-11388 (1996).

Naldini et al., In vivo gene delivery and stable transduction of nondividing cells by a lentiviral vector, Science, vol. 272, pp. 263-267 (1996).

Nightingale et al., Transient gene expression by nonintegrating lentiviral vectors, Mol. Ther., vol. 13, pp. 1121-1132 (2006).

Penn, Major Histocompatibility Complex (MHC), Encyclopedia of Life Sciences, John Wiley & Sons (2005).

Polak et al., In Situ Hybridization: Principles and Practice, Oxford University Press (1990).

Polic et al., Lack of MHC class I complex expression has no effect on spread and control of cytomegalovirus infection in vivo, J. Gen. Virol., 77(Pt. 2): 217-25 (Feb. 1996).

Roe et al., DNA Isolation and Sequencing: Essential Techniques, John Wiley & Sons (1996).

Sambrook et al., Molecular Cloning: a Laboratory Manual, Cold Harbor Laboratory, 2nd edition (1989).

Segura et al., Identification of host proteins associated with retroviral vector particles by proteomic analysis of highly purified vector preparations, J. Virol., 82(3):1107-17 (2008).

Shiina et al., The HLA genomic loci map: expression, interaction, diversity and disease, J Human Genetic, vol. 54, pp. 15-39 (2009).

Voelkel et al., Protein transduction from retroviral Gag precursors, Proc. National Acad. Sci. USA, vol. 107, No. 17, pp. 7805-7810 (2010).

* cited by examiner

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide corresponding to CRISPR RNA
      (crRNA) recognising exon 1 of beta2M

<400> SEQUENCE: 1
accgagtagc gcgagcacag cta                                              23

<210> SEQ ID NO 2
<211> LENGTH: 23
<212> TYPE: DNA
<213> ORGANISM: Artificial Sequence
<220> FEATURE:
<223> OTHER INFORMATION: Oligonucleotide corresponding to crRNA
      recognising exon 1 of beta2M

<400> SEQUENCE: 2
aaactagctg tgctcgcgct act                                              23

<210> SEQ ID NO 3
<211> LENGTH: 24
<212> TYPE: DNA
<213> ORGANISM: Artificial Sequence
<220> FEATURE:
<223> OTHER INFORMATION: Primer flanking the crRNA site in the beta2M
      gene

<400> SEQUENCE: 3
tacagacagc aaactcaccc agtc                                             24

<210> SEQ ID NO 4
<211> LENGTH: 24
<212> TYPE: DNA
<213> ORGANISM: Artificial Sequence
<220> FEATURE:
<223> OTHER INFORMATION: Primer flanking the crRNA site in the beta2M
```

```
        gene

<400> SEQUENCE: 4
agaacttgga gaagggaagt cacg                                          24
```

VECTOR PRODUCTION

CROSS-REFERENCE TO RELATED APPLICATIONS

This Application is a continuation of U.S. patent application Ser. No. 15/325,124, filed on Jan. 10, 2017 (§ 371(c) date), which is the U.S. National Phase of International Application No. PCT/162015/055286, filed on Jul. 13, 2015, which claims priority to United Kingdom Patent Application No. 1412494.5, filed on Jul. 14, 2014.

INCORPORATION BY REFERENCE OF MATERIAL SUBMITTED ELECTRONICALLY

This application incorporates by reference in its entirety a computer-readable nucleotide/amino acid sequence listing identified as one 1,287 bytes ASCII (text) file named "51564A_SeqListing.txt," created Jan. 7, 2021.

FIELD OF THE INVENTION

The present invention relates to cells that display decreased levels of surface-exposed antigens. More specifically, the invention relates to the genetic engineering of cells to decrease the expression of major histocompatibility complex class I (MHC-I) on the surface of the cells. In particular, the invention relates to the use of such cells in the production of enveloped viral particles.

BACKGROUND TO THE INVENTION

Gene therapy involves the incorporation of genetic material into a cell to treat or prevent disease. The genetic material may supplement defective genes with functional copies of those genes, inactivate improperly functioning genes or introduce new therapeutic genes to a cell.

Delivery of genetic material to a cell may be achieved through use of vectors which facilitate the transfer of nucleic acids. Viruses may be engineered to deliver a nucleotide of interest (NOI) to a target cell and are commonly employed as vectors in gene therapy. Viruses that have been used in gene therapy to date include retroviruses, adenoviruses (AdV), adeno-associated viruses (AAV), herpes simplex viruses (HSV) and vaccinia viruses.

Retroviruses, for example α-retroviruses, γ-retroviruses, lentiviruses and spumaviruses, are particularly useful for gene therapy as they permit stable integration of the corrective genetic material into the target cell. Therapeutic benefits have already been achieved in clinical trials based on γ-retrovirus-derived vectors for Adenosine Deaminase Severe Combined Immunodeficiency (ADA-SCID; Aiuti, A. et al. (2009) *N. Engl. J. Med.* 360: 447-58), X-linked Severe Combined Immunodeficiency (SCID-X1; Hacein-Bey-Abina, S. et al. (2010) *N. Engl. J. Med.* 363: 355-64) and Wiskott-Aldrich syndrome (WAS; Boztug, K. et al. (2010) *N. Engl. J. Med.* 363: 1918-27). In addition, lentiviral vectors have been employed as delivery vehicles in the treatment of X-linked adrenoleukodystrophy (ALD; Cartier, N. et al. (2009) *Science* 326: 818-23), and very recently for metachromatic leukodystrophy (MLD; Biffi, A. et al. (2013) *Science* 341: 1233158) and WAS (Aiuti, A. et al. (2013) *Science* 341: 1233151). In pre-clinical studies, lentiviral vectors have also been administered intravenously for liver-directed gene therapy of haemophilia in mice and dog models of the disease (Cantore A. et al., Blood 2012; Matsui H. et al., Mol Ther 2011; Cantore A. et al. Science Translational Medicine 2015 7: 277ra28).

A significant problem associated with the use of viral vectors in gene therapy, however, is their recognition by the target organism's immune system. In the case of enveloped viral vector particles (e.g. retroviral vector particles), membrane-bound proteins that are displayed on the surface of the viral envelope may be recognised and the viral particle itself may be neutralised. Furthermore, on infecting a target cell, the viral envelope becomes integrated with the cell membrane and as a result viral envelope proteins may become displayed on or remain in close association with the surface of the cell. The immune system may therefore also target the cells which the viral vector particles have infected. Both effects may lead to a reduction in the efficacy of NOI delivery by viral vectors.

A viral particle envelope typically originates in a membrane of the producer cell. Therefore, membrane proteins that are expressed on the cell membrane from which the viral particle buds may be incorporated into the viral envelope. The major histocompatibility complex class I (MHC-I) is one such cell membrane protein and, because it is highly polymorphic in nature, it is furthermore a major target of the body's immune response (McDevitt H. O. (2000) *Annu. Rev. Immunol.* 18: 1-17).

MHC-I molecules exposed on the plasma membrane of retroviral vector producing cells are incorporated in the viral particle envelope during the process of vector budding. These MHC-I molecules derived from the producer cells and incorporated in the viral particles can in turn be transferred to the plasma membrane of transduced cells. Alternatively, the MHC-I molecules may remain in close association with the transduced cell membrane as a result of the tendency of viral particles to absorb and remain bound to the target cell membrane.

The presence of exogenous MHC-I molecules on or close to the plasma membrane of transduced cells may elicit an alloreactive immune response in humans and experimental animal models. This may lead to immune-mediated killing or phagocytosis of transduced cells either upon ex vivo gene transfer followed by administration of the transduced cells to the subject, or upon direct in vivo administration of the viral particles. Furthermore, in the case of in vivo administration of MHC-I bearing viral particles into the bloodstream, the viral particles may be neutralised by pre-existing MHC-I specific antibodies before reaching their target cells.

SUMMARY OF THE INVENTION

We have generated genetically engineered cells that may be used for the production of enveloped viral particles (e.g. retroviral vector particles) that are substantially devoid of surface-exposed MHC-I molecules. Surprisingly, we have shown that the absence of surface-exposed MHC-I molecules does not significantly affect the ability of these cells to produce enveloped viral particles. In particular, we have unexpectedly shown that the enveloped viral particles are produced in comparable titres and yields, and do not exhibit diminished infectivity in comparison to producer cells that display surface-exposed MHC-I. Enveloped viral particles produced with these cells will elicit fewer unwanted immune responses during gene therapy, and provide for greater efficacy and safety.

In one aspect, the present invention provides an enveloped viral particle producer cell, wherein the cell is genetically engineered to decrease expression of MHC-I on the surface of the cell.

In another aspect, the present invention provides an enveloped viral particle packaging cell, wherein the cell is genetically engineered to decrease expression of MHC-I on the surface of the cell.

In one embodiment, the enveloped viral particle packaging or producer cell comprises a genetically engineered disruption of a gene encoding β2-microglobulin (β2M). In another embodiment, the cell comprises a genetically engineered disruption of one or more genes encoding an MHC-I α chain. The cell may comprise genetically engineered disruptions in all copies of the gene encoding β2-microglobulin. The cell may comprise genetically engineered disruptions in all copies of the genes encoding an MHC-I α chain. The cell may comprise both genetically engineered disruptions of genes encoding β2-microglobulin and genetically engineered disruptions of genes encoding an MHC-I α chain.

The expression of MHC-I on the surface of the cell may be decreased such that the cell is substantially devoid of surface-exposed MHC-I molecules.

The term viral particle "producer cell" includes a cell that produces viral particles, after transient transfection, stable transfection or vector transduction of all the elements necessary to produce the viral particles or any cell engineered to stably comprise the elements necessary to produce the viral particles.

The term "packaging cell" includes a cell which contains some or all of the elements necessary for packaging an infectious recombinant virus. The packaging cell may lack a recombinant viral vector. Typically, such packaging cells contain one or more vectors which are capable of expressing viral structural proteins. Cells comprising only some of the elements required for the production of enveloped viral particles are useful as intermediate reagents in the generation of viral particle producer cell lines, through subsequent steps of transient transfection, transduction or stable integration of each additional required element. These intermediate reagents are encompassed by the term "packaging cell". Parental cells to be subsequently used for the generation of enveloped viral particle producer or packaging cell lines, in which the expression of MHC-I on the surface of the cell has been decreased are also encompassed by the present invention.

Viral particles referred to herein encompass replication-competent or -defective viruses, viral vectors derived therefrom, and which may or may not comprise a nucleotide or interest.

In one embodiment, the enveloped viral particle producer or packaging cell is derived from a HEK-293 cell.

In one embodiment, the enveloped viral vector particle is derived from a retrovirus, herpes simplex virus, vaccinia virus, hepadnavirus, togavirus, flavivirus, arenavirus, coronavirus, orthomyxovirus, paramyxovirus, bunyavirus, bornavirus, rhabdovirus or filovirus.

In one embodiment, the enveloped viral vector particle is derived from a retrovirus, herpes simplex virus or vaccinia virus.

In one embodiment, the enveloped viral particle is derived from HIV.

In another aspect, the invention provides a population of enveloped viral particle producer or packaging cells of the invention.

In one embodiment, at least about 50%, 60%, 70%, 75%, 80%, 85%, 90%, 95%, 96%, 97%, 98%, 99% or 100% of the cells in the population have been genetically engineered according to the present invention.

In another aspect, the invention provides the use of the enveloped viral particle producer or packaging cell of the invention for the production of enveloped viral particles. Preferably, the enveloped viral particles are substantially devoid of surface-exposed MHC-I molecules.

In another aspect, the invention provides a method of producing enveloped viral particles comprising the steps of:
a) providing an enveloped viral particle producer cell according to the invention; and
b) culturing the cell under conditions suitable for the production of the enveloped viral vector particles.

In another aspect, the invention provides an enveloped viral particle produced by the enveloped viral particle production method of the invention.

In another aspect, the invention provides an enveloped viral particle comprising a decreased number of surface-exposed MHC-I molecules. The number of surface-exposed MHC-I molecules may be decreased such that the immune response to the MHC-I is decreased to a therapeutically relevant degree.

Preferably, the enveloped viral vector particle is substantially devoid of surface-exposed MHC-I molecules.

The enveloped viral particle of the invention may be derived from a retrovirus, herpes simplex virus, vaccinia virus, hepadnavirus, togavirus, flavivirus, arenavirus, coronavirus, orthomyxovirus, paramyxovirus, bunyavirus, bornavirus, rhabdovirus or filovirus.

The enveloped viral vector particle may be derived from a retrovirus, herpes simplex virus or vaccinia virus.

The enveloped viral vector particle may be derived from HIV.

Preferably, the enveloped viral particles of the invention are used for protein transfer (Bobis-Wozowicz S. et al., Sci Rep. 2014; Voelkel C. et al., Proc Natl Acad Sci USA. 2010; Maetzig T. et al., Curr Gene Ther. 2012).

Preferably, the enveloped viral particle comprises a nucleotide of interest (NOI). Preferably, the enveloped viral particle is an attenuated virus, for example a replication deficient virus.

In another aspect, the invention provides a population of enveloped viral particles of the invention.

In one embodiment, at least about 50%, 60%, 70%, 75%, 80%, 85%, 90%, 95%, 96%, 97%, 98% or 99% of the particles in the population originate from an enveloped viral particle producer cell of the invention. In one embodiment, 100% of the particles in the population originate from an enveloped viral particle producer cell of the invention. In one embodiment, the particles in the population substantially do not comprise surface-exposed MHC-I.

In another aspect, the invention provides a cell transduced by the enveloped viral particle of the invention. The cell may be a mammalian cell, for example a primate cell or a human cell.

In another aspect, the invention provides a pharmaceutical composition comprising the enveloped viral particle of the invention or the transduced cell of the invention, and a pharmaceutically acceptable carrier, diluent or excipient.

In another aspect, the invention provides the enveloped viral particle of the invention for use in therapy. The enveloped viral particle of the invention may be used in gene therapy.

In another aspect, the invention provides the transduced cell of the invention for use in therapy. The transduced cell of the invention may be used in gene therapy.

In another aspect, the invention provides a method of gene therapy comprising transducing a cell with the enveloped viral particle of the invention.

In one embodiment, the transduction is carried out ex vivo.

In another aspect, the invention provides a method of gene therapy comprising administering the enveloped viral particle of the invention or the transduced cell of the invention to a subject in need thereof.

In another aspect, the invention provides the enveloped viral particle of the invention for use as a vaccine.

In another aspect, the invention provides a method of vaccination comprising administering the enveloped viral particle of the invention to a subject in need thereof.

DESCRIPTION OF THE DRAWINGS

FIG. 1

Flow cytometry analysis (contour plots with outliers) of lentiviral vector (LV) packaging cell line (A-D) or HEK-293T cells (E-H), untreated, CRISPR/Cas9-treated, β2M+ or β2M− sorted as indicated, performed one month after FACS sorting. Cells were stained with PE-conjugated anti-human β2M and APC-conjugated pan anti-human MHC-I.

FIG. 2

Percentage of β2M alleles with non-homologous end joining (NHEJ), determined by a mismatch-selective endonuclease assay (Cel1 assay) in lentiviral vector (LV) packaging cells (A) or HEK-293 T cells (B) untreated (UNT), CRISPR/Cas9-treated, β2M+ or β2M− sorted as indicated, performed one month after FACS sorting.

FIG. 3

Titer (A), particles (B) and infectivity (C) of lentiviral vector (LV) produced in β2M+ or β2M− HEK-293T cells, as indicated, by transient transfection (n=3, p=0.1000 for titer, p=0.3758 for particles, p=0.1157 for infectivity). Particles (D) of LV produced by β2M+ or β2M− packaging cells 3 days after induction with 1 μg/mL doxycycline (n=4, p=0.1010).

FIG. 4

Western blot analysis on protein extracts from lentiviral vector (LV) batches produced by β2M+ (+) or β2M− (−) producer cells.

FIG. 5

Proliferation assay (A) based on tritiated thymidine incorporation quantitated as counts per minute (CPM). Data are mean and SEM (n=3). Stimulation index (B) calculated as the ratio between CPM of the experimental condition (CD4$^+$ T-cells incubated with dendritic cells (DCs) transduced with lentiviral vectors (LVs) produced by β2M+ (+) or β2M− (−) cells) and the control condition (CD4$^+$ T-cells incubated with untransduced DCs).

DETAILED DESCRIPTION OF THE INVENTION

Various preferred features and embodiments of the present invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F., and Maniatis, T. (1989) *Molecular Cloning: A Laboratory Manual*, 2nd Edition, Cold Spring Harbor Laboratory Press; Ausubel, F. M. et al. (1995 and periodic supplements) *Current Protocols in Molecular Biology*, Ch. 9, 13 and 16, John Wiley & Sons; Roe, B., Crabtree, J., and Kahn, A. (1996) *DNA Isolation and Sequencing: Essential Techniques*, John Wiley & Sons; Polak, J. M., and McGee, J. O'D. (1990) *In Situ Hybridization: Principles and Practice*, Oxford University Press; Gait, M. J. (1984) *Oligonucleotide Synthesis: A Practical Approach*, IRL Press; and Lilley, D. M., and Dahlberg, J. E. (1992) *Methods in Enzymology: DNA Structures Part A: Synthesis and Physical Analysis of DNA*, Academic Press. Each of these general texts is herein incorporated by reference.

In one aspect, the present invention provides an enveloped viral particle producer cell, wherein the cell is genetically engineered to decrease expression of MHC-I on the surface of the cell.

In another aspect, the present invention provides an enveloped viral particle packaging cell, wherein the cell is genetically engineered to decrease expression of MHC-I on the surface of the cell.

Decreased expression of MHC-I on the surface of the cell refers to a decrease in the number of MHC-I molecules that are expressed on the surface of the cell that has been genetically engineered, in comparison to the number of MHC-I molecules that are expressed on the surface of a cell lacking the genetic engineering, but under otherwise substantially identical conditions.

The expression of MHC-I on the surface of the cell may be decreased such that the number of surface-exposed MHC-I molecules is, for example, less than about 50%, 40%, 30%, 25%, 20%, 15%, 10%, 5%, 4%, 3%, 2% or 1% of the number of surface-exposed MHC-I molecules that are displayed in the absence of the genetic engineering. In one embodiment, the expression of MHC-I on the surface of the cell is decreased such that the number of surface-exposed MHC-I molecules is 0% of the number of surface-exposed MHC-I molecules that are displayed in the absence of the genetic engineering.

The expression of MHC-I on the surface of the cell is preferably decreased such that the cell is substantially devoid of surface-exposed MHC-I molecules.

By "substantially devoid" it is to be understood that there is a substantial decrease in the number of MHC-I molecules that are expressed on the surface of the cell that has been genetically engineered, in comparison to the number of MHC-I molecules that are expressed on the surface of a cell lacking the genetic engineering, such that the immune response to MHC-I on enveloped viral particles produced by the cell is decreased to a therapeutically useful degree.

In another aspect, the invention provides an enveloped viral particle producer or packaging cell, wherein the cell comprises a genetically engineered disruption of a gene encoding β2-microglobulin.

In another aspect, the invention provides an enveloped viral particle producer or packaging cell, wherein the cell comprises a genetically engineered disruption of a gene encoding an MHC-I α chain.

In one aspect, the invention provides a population of enveloped viral particle producer or packaging cells of the invention.

Preferably, at least about 50%, 60%, 70%, 75%, 80%, 85%, 90%, 95%, 96%, 97%, 98%, 99% or 100% of the cells in the population do not comprise surface-exposed MHC-I.

Methods for quantifying protein expression of cell surface-exposed proteins in a population of cells are known in the art. Suitable methods include flow cytometry, fluorescence-activated cell sorting (FACS) and fluorescence microscopy.

For example, a population of cells may be contacted with an antibody specific for MHC-I. The antibody may be labelled to enable its detection. The antibody may be directly conjugated to a reporter moiety (e.g. a fluorescent label). Alternatively, a secondary antibody, conjugated to a reporter moiety and specific for the first antibody, may be contacted with the population of cells. Suitable reporter moieties are known in the art and include, for example, Alexa Fluor and BODIPY-based fluorescent labels. Once the population of cells has been contacted with the antibody, the population may be analysed using a technique suitable to allow quantification of protein expression on individual cells, such as flow cytometry. The analysis is carried out without lysing the cells.

The method for quantifying protein expression of cell surface-exposed proteins may also enable sorting of the population of cells to produce a population of cells enriched for a specific characteristic (e.g. to produce a population of cells enriched in cells that do not comprise surface-exposed MHC-I). For example, fluorescence-activated cell sorting (FACS) enables such enrichment to be performed.

Similar methods may be applied for quantifying protein expression of cell surface-exposed proteins on single cells. For example, the method may employ microfluidic approaches.

Major Histocompatibility Complex Class I

The major histocompatibility complex class I (MHC-I) is a heterodimeric membrane protein that is displayed on the outer leaflet of the cell membrane (Penn, D. J. (2002) Major Histocompatibility Complex (MHC) eLS, John Wiley & Sons, http COLON-SLASH-SLASH www.els.net/ [DOI: 10.1038/npg.els.0000919]). MHC-I functions to bind and display peptide fragments of proteins to the extracellular environment where they may be recognised by CD8+ cytotoxic T cells. Peptide fragments generated from normal cellular proteins will not activate cytotoxic T cells due to central and peripheral tolerance mechanisms. However, foreign peptides (e.g. those originating from viral proteins) will cause activation of an immune response to destroy the cell.

An allogeneic MHC-I protein itself may be recognised by the immune system. For example, antibodies may bind MHC-I epitopes directly. As a result, cells and enveloped viruses that comprise MHC-I proteins originating from an allogeneic source may be targeted and neutralised by the immune system.

Human MHC-I is also referred to as human leukocyte antigen class I (HLA-I) and is expressed on almost all nucleated cells. HLA-I consists of two polypeptide chains, an HLA-I heavy chain ($\alpha$ chain) and $\beta$2 microglobulin ($\beta$2M). The HLA-I $\alpha$ chain and $\beta$2M are linked non-covalently.

The HLA-I $\alpha$ chain is polymorphic. Six HLA-I $\alpha$ chains have been identified to date, including three classical, highly polymorphic $\alpha$ chains (HLA-A, HLA-B and HLA-C) and three non-classical, less polymorphic (HLA-E, HLA-F and HLA-G) $\alpha$ chains. The skilled person would readily be able to determine nucleic acid sequences of HLA-I $\alpha$ chains. For example, the HLA-I $\alpha$ chains may be identified in a genome sequence using their location within the major histocompatibility complex region of the chromosome (Penn, D. J. (2002) *Major Histocompatibility Complex (MHC)* eLS, John Wiley & Sons, http COLON-SLASH-SLASH www.els.net/ [DOI: 10.1038/npg.els.0000919]).

Nucleic acid sequences encoding $\beta$2M are known in the art. For example, a nucleic acid sequence of human $\beta$2M is deposited as GenBank Accession No. NM_004048.

The skilled person will understand that the present invention is applicable to variants of MHC-I sequences, such as polymorphisms of these sequences (e.g. HLA-I $\alpha$ chain sequences and $\beta$2M sequences). For example, variants of MHC-I sequences may include single nucleotide polymorphisms (SNPs) or multiple SNPs.

Genetic Engineering of MHC-I

The enveloped viral particle producer or packaging cell of the invention is genetically engineered to decrease expression of MHC-I on the surface of the cell.

Methods for genetic engineering to decrease protein expression are known in the art. For example, this may be achieved by targeted gene knockout. To decrease protein expression, the gene encoding the protein itself or its regulatory sequence (e.g. its promoter) may be knocked out. Knockout may be achieved by deletion of a section of the coding nucleic acid sequence, which may delete a section of the protein essential for expression or stability, or alter the reading frame of the coding sequence. Suitable methods for targeted gene knockout include use of zinc finger nucleases (ZFNs), transcription activator-like effector nucleases (TALENs) and CRISPR/Cas-based RNA-guided nucleases (Gaj, T. et al. (2013) *Trends Biotechnol.* 31: 397-405).

For example, the CRISPR/Cas9 RNA-guided nuclease may be used to catalyse a double strand break at a specific locus in the genome if provided with appropriate RNA guides designed to bind that locus. Cas9 and the guide RNA may be delivered to a target cell by transfection of vectors encoding the protein and RNA. Cells attempt to repair any double strand breaks in their DNA using the non-homologous end joining (NHEJ) pathway. This is an error-prone mechanism which inserts random nucleotides and often disrupts the reading frame of the targeted gene.

Alternatively, the genetic engineering to decrease protein expression may be accomplished using RNAi techniques, or microRNA or antisense RNA to suppress expression of the target gene.

Once the targeted gene knockout or suppression of expression approach has been carried out, the resulting population of cells may be screened to select and enrich for those cells exhibiting the phenotype of interest, for example decreased expression of surface-exposed MHC-I. Suitable techniques for screening and enrichment are known in the art and include flow cytometry and fluorescence-activated cell sorting (FACS).

In one embodiment, the enveloped viral particle producer or packaging cell comprises a genetically engineered disruption of a gene encoding $\beta$2-microglobulin. $\beta$2-microglobulin stabilises MHC-I, thus cells deficient in $\beta$2-microglobulin will exhibit decreased expression of MHC-I on the surface of the cell. The cell may comprise genetically engineered disruptions in all copies of the gene encoding $\beta$2-microglobulin.

In another embodiment, the cell comprises a genetically engineered disruption of a gene encoding an MHC-I $\alpha$ chain. The cell may comprise genetically engineered disruptions in all copies of the gene encoding an MHC-I $\alpha$ chain.

The cell may comprise both genetically engineered disruptions of genes encoding $\beta$2-microglobulin and genetically engineered disruptions of genes encoding an MHC-I $\alpha$ chain.

Vectors

A vector is a tool that allows or facilitates the transfer of an entity from one environment to another. The viral particles of the present invention may be vectors.

The viral vector particles of the invention are enveloped viral particles.

An enveloped viral particle comprises an outer lipid bilayer membrane. Numerous enveloped viruses are known in the art, including retrovirus, herpes simplex virus, vaccinia virus, hepadnavirus, togavirus, flavivirus, arenavirus, coronavirus, orthomyxovirus, paramyxovirus, bunyavirus, bornavirus, rhabdovirus and filovirus Retroviral and Lentiviral Vectors A retroviral vector may be derived from or may be derivable from any suitable retrovirus. A large number of different retroviruses have been identified. Examples include murine leukaemia virus (MLV), human T-cell leukaemia virus (HTLV), mouse mammary tumour virus (MMTV), Rous sarcoma virus (RSV), Fujinami sarcoma virus (FuSV), Moloney murine leukaemia virus (Mo-MLV), FBR murine osteosarcoma virus (FBR MSV), Moloney murine sarcoma virus (Mo-MSV), Abelson murine leukaemia virus (A-MLV), avian myelocytomatosis virus-29 (MC29) and avian erythroblastosis virus (AEV). A detailed list of retroviruses may be found in Coffin, J. M. et al. (1997) *Retroviruses*, Cold Spring Harbour Laboratory Press, 758-63.

Retroviruses may be broadly divided into two categories, "simple" and "complex". Retroviruses may be even further divided into seven groups. Five of these groups represent retroviruses with oncogenic potential. The remaining two groups are the lentiviruses and the spumaviruses. A review of these retroviruses is presented in Coffin, J. M. et al. (1997) *Retroviruses*, Cold Spring Harbour Laboratory Press, 758-63.

The basic structure of retrovirus and lentivirus genomes share many common features such as a 5' Long Terminal Repeats (LTR) and a 3' LTR. Between or within these are located a packaging signal to enable the genome to be packaged, a primer binding site, integration sites to enable integration into a host cell genome, and gag, pol and env genes encoding the packaging components—these are polypeptides required for the assembly of viral particles. Lentiviruses have additional features, such as rev and RRE sequences in HIV, which enable the efficient export of RNA transcripts of the integrated provirus from the nucleus to the cytoplasm of an infected target cell.

In the provirus, these genes are flanked at both ends by regions called LTRs. The LTRs are responsible for proviral integration and transcription. LTRs also serve as enhancer-promoter sequences and can control the expression of the viral genes.

The LTRs themselves are identical sequences that can be divided into three elements: U3, R and U5. U3 is derived from the sequence unique to the 3' end of the RNA. R is derived from a sequence repeated at both ends of the RNA. U5 is derived from the sequence unique to the 5' end of the RNA. The sizes of the three elements can vary considerably among different retroviruses.

In a defective retroviral vector genome gag, pol and env may be absent or not functional.

In a typical retroviral vector, at least part of one or more protein coding regions essential for replication may be removed from the virus. This makes the viral vector replication-defective. Portions of the viral genome may also be replaced by a library encoding candidate modulating moieties operably linked to a regulatory control region and a reporter moiety in the vector genome in order to generate a vector comprising candidate modulating moieties which is capable of transducing a target host cell and/or integrating its genome into a host genome.

Lentivirus vectors are part of the larger group of retroviral vectors. A detailed list of lentiviruses may be found in Coffin, J. M. et al. (1997) *Retroviruses*, Cold Spring Harbour Laboratory Press, 758-63. Briefly, lentiviruses can be divided into primate and non-primate groups. Examples of primate lentiviruses include but are not limited to human immunodeficiency virus (HIV), the causative agent of human acquired immunodeficiency syndrome (AIDS); and simian immunodeficiency virus (SIV). Examples of non-primate lentiviruses include the prototype "slow virus" visna/maedi virus (VMV), as well as the related caprine arthritis-encephalitis virus (CAEV), equine infectious anaemia virus (EIAV), and the more recently described feline immunodeficiency virus (FIV) and bovine immunodeficiency virus (BIV).

The lentivirus family differs from retroviruses in that lentiviruses have the capability to infect both dividing and non-dividing cells (Lewis, P et al. (1992) *EMBO J.* 11: 3053-8; Lewis, P. F. et al. (1994) *J. Virol.* 68: 510-6). In contrast, other retroviruses, such as MLV, are unable to infect non-dividing or slowly dividing cells such as those that make up, for example, muscle, brain, lung and liver tissue.

A lentiviral vector, as used herein, is a vector which comprises at least one component part derivable from a lentivirus. Preferably, that component part is involved in the biological mechanisms by which the vector infects cells, expresses genes or is replicated.

The lentiviral vector may be a "primate" vector. The lentiviral vector may be a "non-primate" vector (i.e. derived from a virus which does not primarily infect primates, especially humans). Examples of non-primate lentiviruses may be any member of the family of lentiviridae which does not naturally infect a primate.

As examples of lentivirus-based vectors, HIV-1- and HIV-2-based vectors are described below.

The HIV-1 vector contains cis-acting elements that are also found in simple retroviruses. It has been shown that sequences that extend into the gag open reading frame are important for packaging of HIV-1. Therefore, HIV-1 vectors often contain the relevant portion of gag in which the translational initiation codon has been mutated. In addition, most HIV-1 vectors also contain a portion of the env gene that includes the RRE. Rev binds to RRE, which permits the transport of full-length or singly spliced mRNAs from the nucleus to the cytoplasm. In the absence of Rev and/or RRE, full-length HIV-1 RNAs accumulate in the nucleus. Alternatively, a constitutive transport element from certain simple retroviruses such as Mason-Pfizer monkey virus can be used to relieve the requirement for Rev and RRE. Efficient transcription from the HIV-1 LTR promoter requires the viral protein Tat.

Most HIV-2-based vectors are structurally very similar to HIV-1 vectors. Similar to HIV-1-based vectors, HIV-2 vectors also require RRE for efficient transport of the full-length or singly spliced viral RNAs.

In one system, the vector and helper constructs are from two different viruses, and the reduced nucleotide homology may decrease the probability of recombination. In addition to vectors based on the primate lentiviruses, vectors based on FIV have also been developed as an alternative to vectors derived from the pathogenic HIV-1 genome. The structures of these vectors are also similar to the HIV-1 based vectors.

Preferably the viral vector used in the present invention has a minimal viral genome.

By "minimal viral genome" it is to be understood that the viral vector has been manipulated so as to remove the non-essential elements and to retain the essential elements in order to provide the required functionality to infect, transduce and deliver a nucleotide sequence of interest to a target host cell. Further details of this strategy can be found in WO 1998/017815.

Preferably the plasmid vector used to produce the viral genome within a host cell/packaging cell will have sufficient lentiviral genetic information to allow packaging of an RNA genome, in the presence of packaging components, into a viral particle which is capable of infecting a target cell, but is incapable of independent replication to produce infectious viral particles within the final target cell. Preferably the vector lacks a functional gag-pol and/or env gene and/or other genes essential for replication.

However, the plasmid vector used to produce the viral genome within a host cell/packaging cell will also include transcriptional regulatory control sequences operably linked to the lentiviral genome to direct transcription of the genome in a host cell/packaging cell. These regulatory sequences may be the natural sequences associated with the transcribed viral sequence (i.e. the 5' U3 region), or they may be a heterologous promoter, such as another viral promoter (e.g. the CMV promoter).

The vectors may be self-inactivating (SIN) vectors in which the viral enhancer and promoter sequences have been deleted. SIN vectors can be generated and transduce non-dividing cells in vivo with an efficacy similar to that of wild-type vectors. The transcriptional inactivation of the long terminal repeat (LTR) in the SIN provirus should prevent mobilisation by replication-competent virus. This should also enable the regulated expression of genes from internal promoters by eliminating any cis-acting effects of the LTR.

The vectors may be integration-defective. Integration defective lentiviral vectors (IDLVs) can be produced, for example, either by packaging the vector with catalytically inactive integrase (such as an HIV integrase bearing the D64V mutation in the catalytic site; Naldini, L. et al. (1996) *Science* 272: 263-7; Naldini, L. et al. (1996) *Proc. Natl. Acad. Sci. USA* 93: 11382-8; Leavitt, A. D. et al. (1996) *J. Virol.* 70: 721-8) or by modifying or deleting essential att sequences from the vector LTR (Nightingale, S. J. et al. (2006) *Mol. Ther.* 13: 1121-32), or by a combination of the above.

HIV-Derived Vectors

HIV-derived vectors for use in the present invention are not particularly limited in terms of HIV strain. Numerous examples of sequences of HIV strains may be found at the HIV Sequence Database (http COLON SLASH SLASH www.hiv.lanl.qov/content/index).

Herpes Simplex Virus (HSV) Derived Vectors

Herpes simplex virus (HSV) is an enveloped double-stranded DNA virus that naturally infects neurons. HSV can accommodate large sections of foreign DNA, which makes it attractive as a vector system, and has been employed as a vector for gene delivery to neurons.

The use of HSV in therapeutic procedures requires the strains to be attenuated so that they cannot establish a lytic cycle. In particular, if HSV vectors are to be used for gene therapy in humans, the NOI is preferably inserted into an essential gene. This is necessary, because if a vector virus encounters a wild type virus, transfer of a heterologous gene to the wild type virus could occur by recombination. However, as long as the NOI is inserted into an essential gene, recombinational transfer would also delete the essential gene in the recipient virus and prevent "escape" of the heterologous gene into the replication competent wild type virus population.

Vaccinia Virus-Derived Vectors

Vaccinia virus is large enveloped virus that has an approximately 190 kb linear, double-stranded DNA genome. Vaccinia virus can accommodate up to approximately 25 kb of foreign DNA, which also makes it useful for the delivery of large genes.

A number of attenuated vaccinia virus strains are known in the art that are suitable for gene therapy applications, for example the MVA and NYVAC strains.

Viral Particle Production

In one aspect, the invention provides the use of the enveloped viral particle producer cell of the invention for the production of enveloped viral particles.

In one embodiment, the enveloped viral vector particles comprise less than about 50%, 40%, 30%, 25%, 20%, 15%, 10%, 5%, 4%, 3%, 2% or 1% of the number of surface-exposed MHC-I molecules that are displayed on particles produced by enveloped viral particle producer cells in the absence of the genetic engineering. In another embodiment, the enveloped viral particles are substantially devoid of surface-exposed MHC-I molecules.

The enveloped viral particle producer cell may comprise the viral genome.

The viral genome is the nucleic acid sequence that is incorporated into the viral particle. The viral genome may be engineered to comprise a nucleotide of interest (NOI).

Accordingly, for use in producing viral particles, the enveloped viral particle producer cell may comprise the viral genome and subsequently cultured under conditions suitable for the production of the enveloped viral particles.

An "enveloped viral particle packaging cell" may, for example, comprise nucleic acid sequences encoding some or all the structural proteins required for viral particle assembly.

Cells comprising only some of the elements required for the production of enveloped viral particles are useful as intermediate reagents in the generation of viral particle producer cell lines, through subsequent steps of transient transfection, transduction or stable integration of each additional required element. These intermediate reagents are encompassed by the packaging cell lines of the invention. Parental cells to be subsequently used for the generation of enveloped viral particle producer or packaging cell lines, in which the expression of MHC-I on the surface of the cell has been decreased represent another embodiment of the invention.

The nucleic acid sequences encoding the components required for production of an infectious enveloped viral particle may be transiently transfected or transduced into or stably maintained (e.g. stably integrated into the cell genome or episomally maintained) within the packaging or producer cell. Alternatively, a combination of transient transfection or transduction and stable maintenance may be used to introduce the nucleic acid sequences into the cell.

Accordingly, the cell of the invention may be transfected or transduced with or engineered to stably integrate by targeted integration a nucleic acid comprising the viral genome to enable production of enveloped viral particles which comprise the viral genome.

The nucleic acid sequences encoding separate components required for production of an infectious enveloped viral particle may be provided to the cell as separate expression cassettes.

In one embodiment, the packaging cell of the invention comprises nucleic acid sequences encoding Gag, Gag/Pol, and/or Env proteins, or functional substitutes thereof. The cell may optionally comprise nucleic acid sequences encoding additional proteins that may be required for retroviral vector particle assembly, for example Rev protein.

Enveloped viral particle producer or packaging cells can be of any suitable cell type that is capable of producing or packaging enveloped viral particles. The cells are preferably mammalian cells, particularly human cells. For example, the enveloped viral particles producer cell may be derived from a parental HEK-293 cell.

Nucleotide of Interest

The vectors e.g., viral particles, of the invention may comprise a nucleotide of interest (NOI).

Preferably, the nucleotide of interest gives rise to a therapeutic effect.

Suitable NOIs include, but are not limited to sequences encoding enzymes, cytokines, chemokines, hormones, antibodies, anti-oxidant molecules, engineered immunoglobulin-like molecules, single chain antibodies, fusion proteins, immune co-stimulatory molecules, immunomodulatory molecules, anti-sense RNA, microRNA, shRNA, siRNA, ribozymes, miRNA target sequences, a transdomain negative mutant of a target protein, toxins, conditional toxins, antigens, tumour suppressor proteins, growth factors, transcription factors, membrane proteins, surface receptors, anti-cancer molecules, vasoactive proteins and peptides, anti-viral proteins and ribozymes, and derivatives thereof (such as derivatives with an associated reporter group). The NOIs may also encode pro-drug activating enzymes.

An example of a NOI is the coagulation factor VIII or factor IX or engineered derivatives thereof, which may be used for gene therapy of haemophilia or the beta-globin chain which may be used for gene therapy of thalassemia/sickle cell disease.

Suitable proteins that can be transferred by viral vector protein transfer include, but are not limited to nucleases, integrases, transposases, enzymes, cytokines, chemokines, hormones, antibodies, anti-oxidant molecules, engineered immunoglobulin-like molecules, single chain antibodies, fusion proteins, immune co-stimulatory molecules, immunomodulatory molecules, a transdomain negative mutant of a target protein, toxins, conditional toxins, antigens, tumour suppressor proteins, growth factors, transcription factors, membrane proteins, surface receptors, anti-cancer molecules, vasoactive proteins and peptides, anti-viral proteins and ribozymes, and derivatives thereof (such as derivatives with an associated reporter group).

Pharmaceutical Composition

The enveloped viral particles or transduced cells of the invention may be formulated for administration to subjects with a pharmaceutically acceptable carrier, diluent or excipient. Suitable carriers and diluents include isotonic saline solutions, for example phosphate-buffered saline, and potentially contain human serum albumin.

Handling of the cell therapy products is preferably performed in compliance with FACT-JACIE International Standards for cellular therapy.

Gene Therapy

In one aspect, the invention provides enveloped viral particles and transduced cells for use in therapy, for example for use in gene therapy. The enveloped viral particles may be referred to as enveloped viral vector particles.

By a "transduced cell" or a cell which has been "transduced by an enveloped viral vector particle", it is to be understood that the nucleic acid (e.g. comprising the NOI) carried by the enveloped viral vector particle has been transferred to the cell. The cell to be transduced is preferably a target cell.

The enveloped viral vector particles of the invention may be administered directly to a subject. The viral vector particles may be engineered to target infection to specific cells in a subject. The viral vector particles may also be engineered to target expression of the NOI to specific cells in a subject. This may be achieved using tissue-specific promoters or nucleic acid sequences which facilitate suppression of NOI expression in specific cells.

The enveloped viral vector particles may also be used to transduce cells that have been removed from the body of a subject as part of an ex vivo gene therapy approach.

The transduced cells may be administered as part of an autologous cell transplant procedure or as part of an allogeneic cell transplant procedure.

By "autologous cell transplant procedure" it is to be understood that the starting population of cells (which are then transduced with the enveloped viral vector particles of the invention) is obtained from the same subject as that to which the transduced cell population is administered. Autologous transplant procedures are advantageous as they avoid problems associated with immunological incompatibility and are available to subjects irrespective of the availability of a genetically matched donor.

By "allogeneic cell transplant procedure" it is to be understood that the starting population of cells (which are then transduced with the enveloped viral vector particles of the invention) is obtained from a different subject as that to which the transduced cell population is administered. Preferably, the donor will be genetically matched to the subject to which the cells are administered to minimise the risk of immunological incompatibility.

Suitable doses of the enveloped viral vector particles or transduced cells are such as to be therapeutically and/or prophylactically effective. The dose to be administered may depend on the subject and condition to be treated, and may be readily determined by a skilled person.

For example, the use may be as part of a haematopoietic stem and/or progenitor cell transplantation procedure.

Haematopoietic stem cell transplantation (HSCT) is the transplantation of blood stem cells derived from the bone marrow (in this case known as bone marrow transplantation) or blood. Stem cell transplantation is a medical procedure in the fields of haematology and oncology, most often performed for people with diseases of the blood or bone marrow, or certain types of cancer.

Many recipients of HSCTs are multiple myeloma or leukaemia patients who would not benefit from prolonged treatment with, or are already resistant to, chemotherapy. Candidates for HSCTs include paediatric cases where the patient has an inborn defect such as severe combined immunodeficiency or congenital neutropenia with defective stem cells, and also children or adults with aplastic anaemia who have lost their stem cells after birth. Other conditions treated with stem cell transplants include sickle-cell disease, myelodysplastic syndrome, neuroblastoma, lymphoma, Ewing's Sarcoma, Desmoplastic small round cell tumour and Hodgkin's disease. More recently non-myeloablative, or so-called "mini transplant", procedures have been developed that require smaller doses of preparative chemotherapy and radiation. This has allowed HSCT to be conducted in the elderly and other patients who would otherwise be considered too weak to withstand a conventional treatment regimen.

The enveloped viral vector particle or transduced cells of the invention may be useful in the treatment of genetic diseases, such as plasma protein deficiencies, metabolic disorders, lysosomal storage disorders, mucopolysaccharidoses, immune deficiencies, haematological disorders, including but not limited to haemophilia, adenosine deaminase severe combined Immunodeficiency, Wiskott-Aldrich syndrome, metachromatic leukodystrophy, globoid leukodystrophy, β-thalassemia, chronic granulomatous disease.

The enveloped viral vector particles or transduced cells of the invention may be useful in the treatment of the disorders listed in WO 1998/005635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the enveloped viral vector particles or transduced cells of the invention may be useful in the treatment of the disorders listed in WO 1998/007859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); anti-inflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the enveloped viral vector particles or transduced cells of the invention may be useful in the treatment of the disorders listed in WO 1998/009985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Method of Treatment

It is to be appreciated that all references herein to treatment include curative, palliative and prophylactic treatment, although in the context of the present invention references to preventing are more commonly associated with prophylactic treatment. The treatment of mammals, particularly humans, is preferred. Both human and veterinary treatments are within the scope of the present invention.

Vaccines

In one aspect, the invention provides an enveloped viral particle of the invention for use as a vaccine. Preferably the enveloped viral particle is not infectious, for example is incapable of infecting a cell.

Attenuated viruses are commonly used in the art as vaccines to provide immunity against infection by the natural, virulent forms of the viruses.

Attenuated viruses for use as vaccines may be produced using the producer cells of the invention as described above, preferably wherein the NOI may be omitted. The producer cells of the invention enable the production of enveloped viral particles that exhibit decreased numbers of surface-exposed MHC-I molecules for use as vaccines. The enveloped viral vector particle for use as a vaccine may be substantially devoid of surface-exposed MHC-I molecules.

A decreased number or lack of surface-exposed MHC-I molecules is advantageous in viruses for use as vaccines, as the viruses will be less likely to be neutralised by antibodies binding to MHC-I.

Additionally, the immune response may react against the allogeneic MHC-I rather than against viral antigens, therefore viral particles substantially devoid of allogeneic MHC-I molecules may be more effective vaccines, by more effectively inducing protective immunity.

The viruses for use as vaccines may be further engineered to express additional proteins on their surfaces or within infected cells. Such proteins may act as antigens for the generation of antibodies or cellular immunity which may further increase the body's immune defences.

EXAMPLES

Example 1

Materials and Methods

β2M Gene Disruption

To generate the eukaryotic expression plasmid encoding for Cas9, the human codon-optimised version of the *Streptococcus pyogenes* Cas9 sequence was excised from the hCas9 plasmid (Addgene, plasmid no. 41815) using XbaI and PmeI. This fragment was then cloned into the pcDNA3.1 plasmid (Invitrogen), which was previously digested with XbaI and EcoRV.

To generate the plasmid encoding for the β2M RNA guide, DNA synthesis was used to create a plasmid containing the sequence of the human U6 promoter followed by the sequence of the transactivating RNA (GeneWix). This plasmid was then digested with BsaI in order to create compatible DNA ends for the following annealed oligonucleotides corresponding to CRISPR RNAs (crRNAs) recognising exon 1 of β2M: 5'-ACCGAGTAGCGCGAGCACAGCTA-3'; 5'-AAACTAGCTGTGCTCGCGCTACT-3'.

Plasmids were delivered into cells (250 ng of Cas9-expressing plasmid plus 50 or 100 ng of guide RNA-expressing plasmid) by calcium phosphate DNA transfection.

Flow Cytometry

All cell suspensions were incubated with FcR Blocking Reagent (Miltenyi) together with PE-conjugated anti-human β2M (BioLegend, clone 2M2) and APC-conjugated pan anti-human MHC-I (Santa Cruz Biotechnology) in phosphate buffered saline, 0.5% bovine serum albumin, ethylenediaminetetraacetic acid (2 mM) (staining solution) for 20 minutes at 4° C. After antibody staining, the cells were washed, re-suspended in staining solution and analysed by flow cytometry (FACSCanto, BD Biosciences).

Mismatch Selective Endonuclease Assay

The mismatch selective endonuclease assay was used to measure the extent of mutations consequent to non-homologous end joining (NHEJ) at the Cas9 target site. Briefly, PCR was performed using primers flanking the crRNA site in the β2M gene (Fw: 5'-TACAGACAGCAAACTCACCCAGTC-3'; Rv: 5'-AGAACTTGGAGAAGGGAAGTCACG-3'). The PCR product was denatured, allowed to re-anneal and digested with Surveyor nuclease assay (Transgenomic). Because this enzyme cuts DNA at sites of duplex distortions, the products of re-annealing between wild type and mutant alleles (carrying mutations or deletions consequent to the nuclease activity) are specifically digested. The reaction products were separated on a Spreadex EL1200 Wide Mini gel (Elchrom Scientific), stained by ethidium bromide and the intensity of the bands was quantified by ImageQuant TL software. The ratio of the uncleaved parental fragment to the two lower migrating cleaved products was calculated using the formula (1-(parental fraction)$^{1/2}$)×100 (Lombardo, A. et al. (2011) *Nat. Methods* 8: 861-9.

Lentiviral Vector (LV) Production

Third-generation lentiviral vectors (LVs) were produced by calcium phosphate transient transfection of 293T cells with the pCCLsin.cPPT.PGK.GFP.pre transfer vector, the packaging plasmid pMDLg/p.RRE, pCMV.REV, the VSV-G envelope plasmid pMD2.G, as previously described (Follenzi, A. et al. (2002) *Methods Mol. Med.* 69: 259-74). 293T cells were seeded 24 hours before transfection in 15 cm dishes. Two hours before transfection, culture medium was replaced with fresh medium. For each dish, a solution containing a mix of the LV genome plasmid, the packaging plasmids pMDLg/pRRE and pCMV.REV, and pMD2.G was prepared using 35 μg, 12.5 μg, 6.25 μg and 9 μg of plasmid DNA, respectively. A 0.1×TE solution (10 mM Tris-HCl, 1 mM EDTA, pH 8.0 in $dH_2O$) and water (1:2) was added to the DNA mix to 1250 μL of final volume. The solution was left on a spinning wheel for 20-30 minutes, then 125 μL of 2.5 M $CaCl_2$ was added. Immediately before transfection, a precipitate was formed by adding 1250 μL of 2×HBS (281 mM NaCl, 100 mM HEPES, 1.5 mM $Na_2HPO_4$, pH 7.12) while the solution was kept agitated on a vortex. The precipitate was immediately added to the culture medium and left on the cells for 14-16 hours and subsequently the culture medium was changed. Supernatant was collected 30 hours after medium change and passed through a 0.22 μm filter (Millipore).

Packaging cells were previously generated starting from 293-T-REx (Invitrogen), stably expressing a tetracycline-regulated transcriptional repressor, stably transfected with plasmids expressing HIV-1 Rev, Gag/Pol and VSV-G under the control of a Tet operator linked to a CMV promoter. Production of LV particles was induced by addition of doxycycline (1 μg/mL) to the culture medium and supernatant was collected after 72 hours and passed through a 0.22 μm filter (Millipore).

LV Titration

One hundred thousand 293T cells were transduced with serial vector dilutions in the presence of polybrene (8 μg/mL). The percentage of GFP positive (GFP+) cells was measured 7 days after transduction by flow cytometry. Titer was expressed as transducing units$_{293T}$ (TU)/mL and calculated using the formula:

$$TU/mL=[(\%\ GFP+cells/100)\times 10^5\times 1/dilution\ factor]$$

Vector particles were measured by HIV-1 Gag p24 antigen immunocapture according to the manufacturer's protocol (NEN Life Science Products). Vector infectivity was calculated as the ratio between titer and particles (TU/ng p24).

Statistical Analysis

Statistical analyses were performed using the Mann-Whitney test at p<0.05 level of significance.

Results

Figure 1:
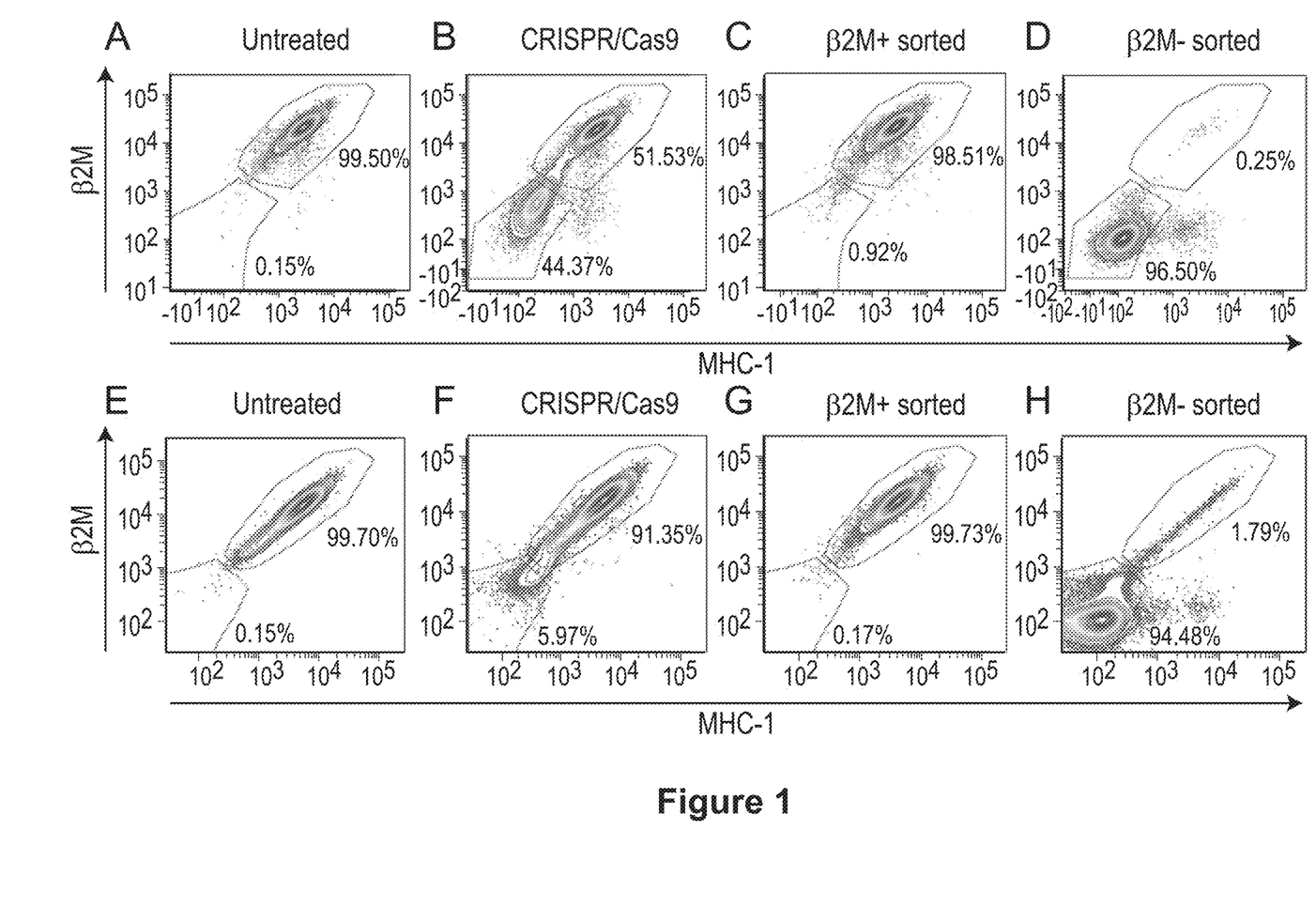

In order to generate cell lines devoid of surface-exposed MHC-I molecules for the production of lentiviral vectors (LVs) devoid of surface-exposed MHC-I molecules, we set out to permanently disrupt the gene encoding for Beta-2-Microglobulin (β2M). Because β2M is a universal component of MHC-I, required for its expression on the cell membrane, by genetically inactivating the β2M gene we aim to impair surface expression of all the highly polymorphic MHC-I molecules, without the need of individually disrupting each of the genes composing the MHC-I (Shiina, T. et al. (2009) *J. Hum. Genet.* 54: 15-39; Adams, E. J. et al. (2013) *Annu. Rev. Immunol.* 31: 529-6). To this aim we used the CRISPR/Cas9 system (Hsu, P. D. (2014) *Cell* 157: 1262-78). Cas9 is an RNA-guided nuclease which is able to perform a DNA double-strand break (DSB) at a pre-determined locus in the genome if provided with appropriate RNA guides designed to bind the desired locus. As a consequence, the cells in which the DSB occurs repair the DNA by the non-homologous end joining (NHEJ) pathway, an error-prone mechanism which inserts random nucleotides and often disrupts the reading frame of the targeted gene (Lombardo, A. et al. (2011) *Nat. Methods* 8: 861-9). We delivered two plasmids, one encoding for the Cas9 nuclease and the other expressing a guide RNA designed to base pair with a sequence in the first exon of the β2M gene, by transient transfection to both a HEK-293-based inducible cell line, previously engineered to produce LV particles, and HEK-293T cells, which are routinely used to produce LV by transient transfection with LV packaging and genome constructs. We have shown by flow cytometry analysis that, while untreated cells are 100% positive for β2M and MHC-I (FIGS. 1A and 1E), up to 44% of the cells treated with Cas9 and the appropriate guide RNA loose β2M and, as a consequence, MHC-I expression on their membrane (FIGS. 1B and 1F). We then enriched for β2M negative (β2M-) cells to almost complete purity (95%) by fluorescence-activated cell sorting (FACS). We have shown that these cells are stable in culture and remain negative for both β2M and MHC-I (FIGS. 1D and 1H). Although the efficiency of β2M disruption was initially lower in HEK-293T cells (6%, FIG. 1F), we were able to easily enrich for the β2M- HEK-293T cells by FACS-sorting (FIGS. 1G and 1H).

Figure 2:
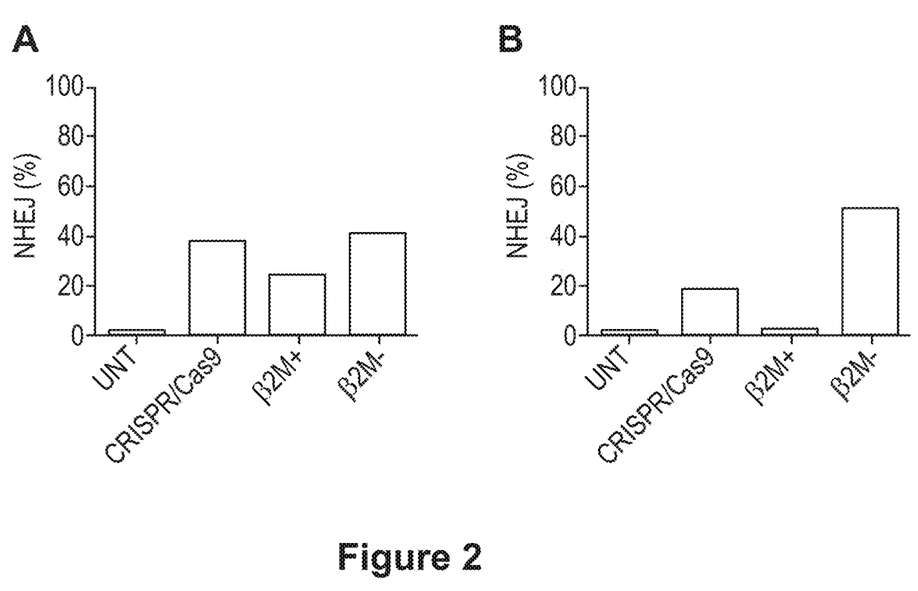

To confirm these results at the genetic level, we analysed the events of NHEJ at the β2M gene by a mismatch-selective endonuclease assay (Cel1 assay; Lombardo, A. et al. (2011) *Nat. Methods* 8: 861-9). We have shown up to 35% of β2M alleles are disrupted in CRISPR/Cas9 treated cells, which increased in β2M- sorted cells, both in 293T cells and the LV packaging cell line (FIG. 2).

Figure 3:
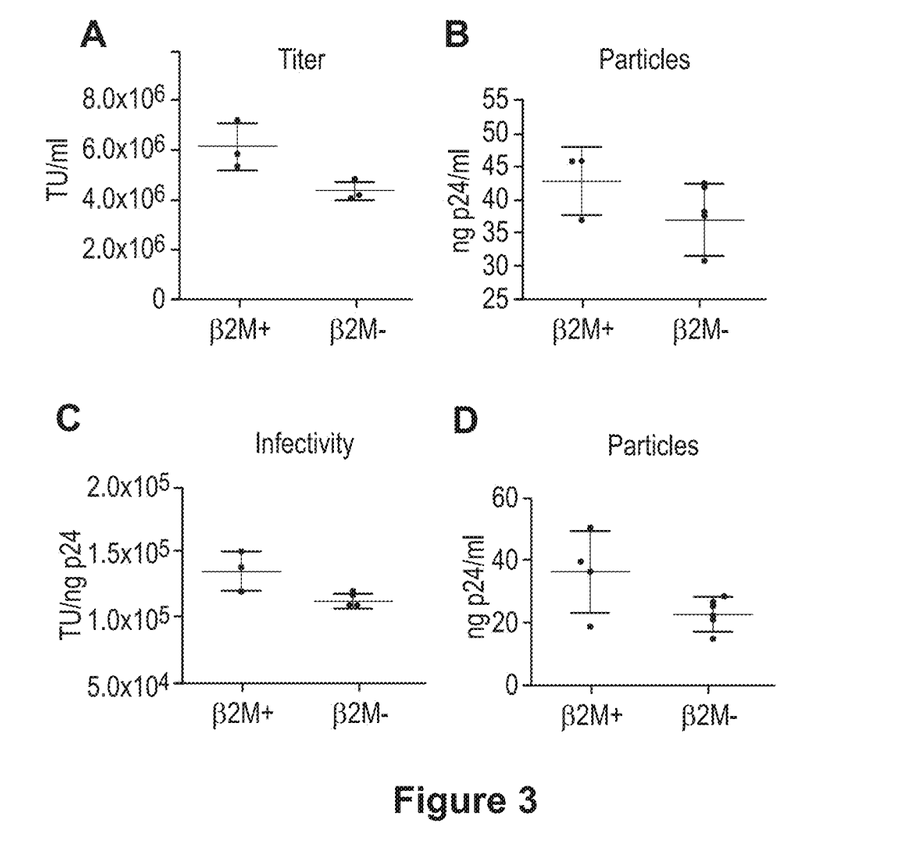

We then evaluated whether β2M- cells retain their capacity to produce LV. To this aim we compared the infectious titer, particle output and infectivity of LVs produced in β2M positive (β2M+) and β2M- 293T cells, upon a standard transient transfection procedure. Our data show that LVs produced in β2M- 293T cells are not significantly different than those produced in β2M+ 293T cells (FIGS. 3A, 3B and 3C). We also induced the production of LVs in β2M+ and β2M- packaging cells and showed similar particle output in LVs collected from the 2 packaging cell lines (FIG. 3D).

Overall these results show efficient disruption of β2M alleles in cells treated with CRISPR/Cas9 and almost complete disappearance of MHC-I molecules from the plasma membrane of β2M- cells. Moreover, we have shown that LVs derived from these β2M- cells have no impairment in their infectivity.

Example 2

Materials and Methods

Human peripheral blood was obtained from healthy donors upon informed consent in accordance with local ethical committee approval (Protocol TIGET03) and with the Declaration of Helsinki. Peripheral blood mononuclear cells (PBMCs) were separated by density gradient centrifugation over Lymphoprep (Fresenius Kabi).

T-Cell Purification and Dendritic Cell (DC) Differentiation

CD3$^+$ T cells were purified from PBMCs by negative selection using the Pan T cell Isolation kit II (Miltenyi Biotech) according to the manufacturer's instructions and frozen. CD14$^+$ monocytes were isolated from PBMCs from the same donor by positive selection using CD14 MicroBeads (Miltenyi Biotech) according to the manufacturer's instructions. Cells were cultured in RPMI 1640 (Corning) supplemented with 10% Fetal Bovine Serum (FBS) (Euroclone), 100 U/mL penicillin/streptomycin (Lonza), 2 mM L-Glutamine (Lonza) at 37° C. in the presence of 10 ng/mL rhIL-4 (R&D Systems) and 100 ng/mL rhGM-CSF (Genzyme) for 7 days to differentiate DCs. Cells on day 2 were transduced with 1 μg p24/mL of lentiviral vector (LV) produced by β2M+ or β2M- cells. Cells on day 6 were matured with 1 μg/mL of LPS (Sigma) for an additional 1 day to generate mature DCs. At day 7, DCs were collected and used to stimulate T cells.

Proliferation of T-Cells

CD3$^+$ T cells were thawed and cultured overnight in RPMI 1640 (Corning) supplemented with 10% FBS (Euroclone), 100 U/mL penicillin/streptomycin (Lonza), 2 mM L-Glutamine (Lonza) and 20 U/mL rhIL-2 (Chiron). T-cells were then stimulated with untransduced DCs or DCs transduced with LVs produced by β2M+ or β2M- cells (10:1 and 5:1 T-cell:DC ratio) in a final volume of 200 μL of IMDM (Sigma) supplemented with 10% FBS (Euroclone), 100 U/mL penicillin/streptomycin (Lonza), 2 mM L-Glutamine (Lonza) for 3 days and then pulsed for 16 h with 1 μCi/well 3H-thymidine.

Western Blot

Total proteins in LV batches were extracted with membrane-protein lysis buffer (150 mM Tris-HCl, 150 mM NaCl, 5 mM EDTA, 1% deoxycholate, 0.1% SDS, 1% Triton-X100) supplemented with PIC (Protease Inhibitor Cocktail; Roche). Samples were resuspended in the lysis solution and incubated at 4° C. for 10 min. Lysates were assayed for protein concentration using Bradford assay (BioRad). 20 μg of proteins were analysed by SDS-PAGE under reducing conditions. For immunoblotting, proteins were transferred to polyvinylidene difluoride (PVDF) membranes using iBlot Gel Transfer stacks (Novex), incubated with the specific antibody followed by peroxidase-conjugated secondary antibodies (ECL Mouse or Rabbit IgG; GE Healthcare), and detected using chemiluminescent reagents (ECL; GE Healthcare) and exposure to autoradiography films. The following antibodies were used: rabbit monoclonal anti-human MHC-I (OriGene Technologies, 1:1000 in TBS, TWEEN®-20 0.1% nonionic surfactant, skim milk powder 5%), mouse monoclonal anti-Gag p24 (NIH AIDS reagent program #3537, 1:1000 in TBS, TWEEN®-20 0.1% nonionic surfactant, skim milk powder 5%).

Results

In order to detect the incorporation of MHC-I in lentiviral vector (LV) particles from the plasma membrane of LV-producer cells, we performed Western blot analysis on proteins extracted from LVs collected by ultracentrifugation from the conditioned medium of β2M+ or β2M– producer cells.

Figure 4:
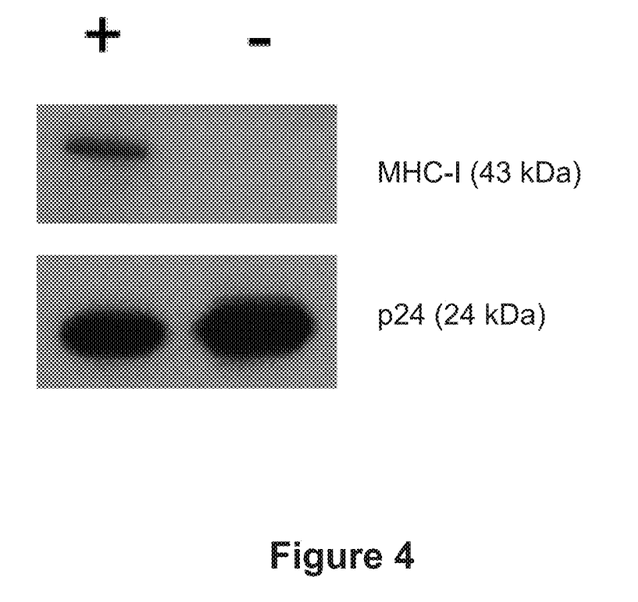

We detected a clear band corresponding to the molecular weight of MHC-I in LVs produced by β2M+ cells, but not in those produced by β2M– cells. Both samples were similarly positive for the capsid Gag p24 protein as expected (FIG. 4).

We then set out to measure the activation of immune cells in response to autologous dendritic cells exposed to LV particles produced by β2M+ or β2M– cells.

Figure 5:
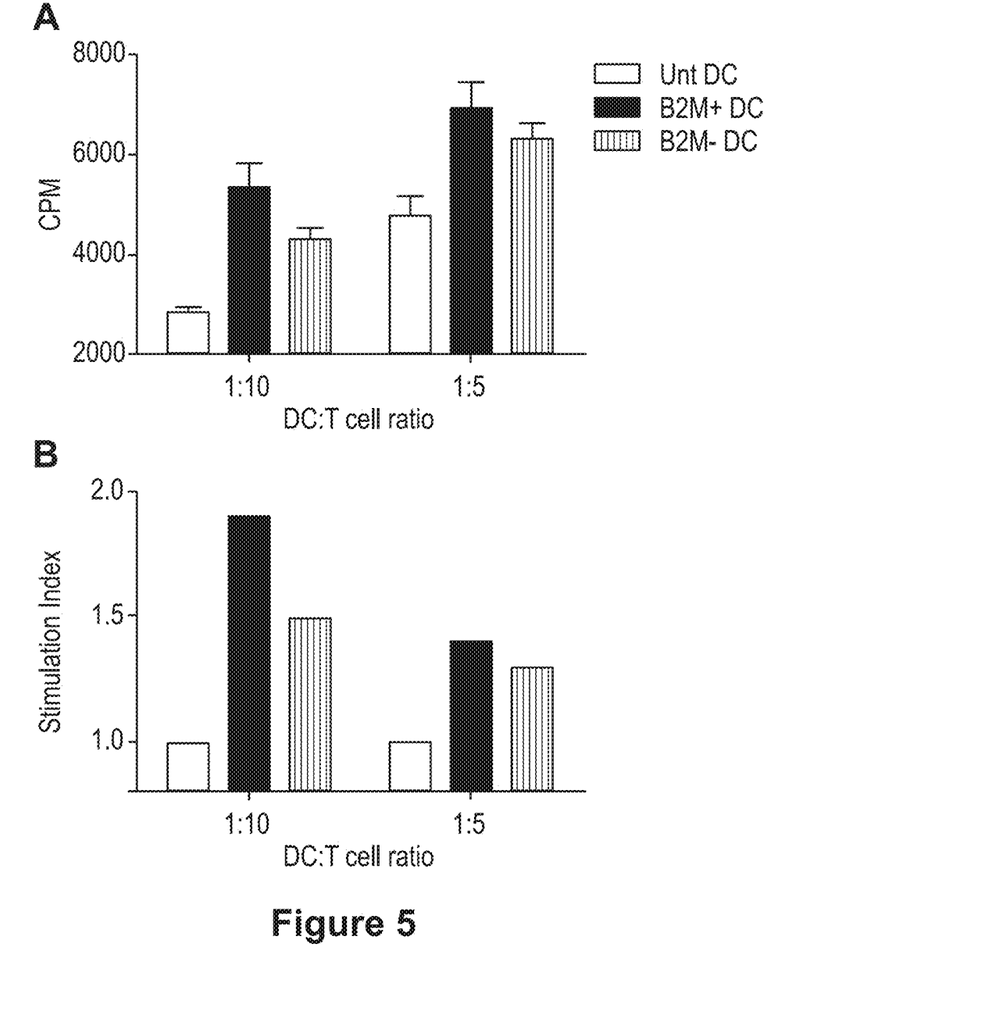

We purified CD3$^+$ T lymphocytes and CD14$^+$ monocytes from peripheral-blood mononuclear cells of healthy donors and subsequently exposed the CD14$^+$ cells to the same amount of LV particles produced by β2M+ or β2M– cells. We then differentiated the transduced monocytes in dendritic cells (DCs) and co-cultured them with the CD3$^+$ lymphocytes from the same donor. We measured T-lymphocyte proliferation by tritiated thymidine incorporation and observed that T lymphocytes proliferate substantially less in response to DCs exposed to LVs produced by β2M– than in response to DCs exposed to LVs produced by β2M+ cells (FIG. 5).

Overall, these data confirm the presence of MHC-I in LV particles produced by parental β2M+ cells and the effective generation of MHC-free LV by β2M– cells. Moreover, these data indicate that MHC-free LV particles and transduced cells are less likely to induce and be targeted by an allo-specific immune response.

All publications mentioned in the above specification are herein incorporated by reference. Various modifications and variations of the described cells, viral vector particles, uses and methods of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention, which are obvious to those skilled in biochemistry and biotechnology or related fields, are intended to be within the scope of the following claims.

The invention claimed is:

1. An enveloped viral particle producer or packaging cell, wherein the producer or packaging cell is genetically engineered to decrease expression of MHC-1 on the surface of the producer or packaging cell, wherein the producer or packaging cell comprises one or more nucleic acid sequences encoding one or more viral particle structural proteins, and wherein:
   (a) the packaging cell lacks a vector encoding a viral genome; whereas
   (b) the producer cell further comprises a vector encoding a viral genome comprising a therapeutic nucleotide of interest.

2. The enveloped viral particle producer or packaging cell of claim 1, wherein the cell comprises a genetically engineered disruption of a gene encoding β2-microglobulin.

3. The enveloped viral particle producer or packaging cell of claim 1, wherein the cell comprises a genetically engineered disruption of one or more genes encoding an MHC-1α chain.

4. The enveloped viral particle producer or packaging cell of claim 1, wherein the cell is a HEK-293 cell or a derivative thereof.

5. The enveloped viral particle producer or packaging cell of claim 4, wherein the cell is a HEK-293T or a HEK-293 T-REx cell.

6. The enveloped viral particle producer or packaging cell of claim 1, wherein the enveloped viral particle is a retrovirus, herpes simplex virus, vaccinia virus, hepadnavirus, togavirus, flavivirus, arenavirus, coronavirus, orthomyxovirus, paramyxovirus, bunyavirus, bornavirus, rhabdovirus, filovirus or derived therefrom.

7. The enveloped viral particle producer or packaging cell of claim 1, wherein the enveloped viral particle is a lentivirus or derived therefrom.

8. The enveloped viral particle producer or packaging cell of claim 1, wherein the therapeutic nucleotide of interest encodes coagulation factor VIII or factor IX, or engineered derivatives thereof; or beta-globin.

9. The enveloped viral particle producer or packaging cell of claim 1, wherein the cell comprises one or more nucleic acid sequences encoding a viral capsid protein and/or a viral envelope protein.

10. The enveloped viral particle producer or packaging cell of claim 1, wherein the viral particle is a retroviral particle, and wherein the cell comprises one or more nucleic acid sequences encoding one or more proteins selected from the group consisting of Gag, Pol and Env.

11. The enveloped viral particle producer or packaging cell of claim 10, wherein the viral particle is a lentiviral particle.

12. The enveloped viral particle producer or packaging cell of claim 11, wherein the cell further comprises a nucleic acid sequence encoding Rev.

13. A method of producing enveloped viral particles comprising the steps:
   (a) providing an enveloped viral particle producer cell according to claim 1; and
   (b) culturing the cell under conditions suitable for the production of the enveloped viral particles.

14. The method of claim 13, wherein the enveloped viral particles are substantially devoid of surface-exposed MHC-1 molecules.

\* \* \* \* \*